United States Patent
Duan

(10) Patent No.: US 6,218,160 B1
(45) Date of Patent: Apr. 17, 2001

(54) SITE-SPECIFIC CONJUGATION OF GLYCOPROTEINS

(75) Inventor: Chuanming Larry Duan, Hockessin, DE (US)

(73) Assignee: Roche Diagnostics Corporation, Indianapolis, IN (US)

( * ) Notice: Subject to any disclaimer, the term of this patent is extended or adjusted under 35 U.S.C. 154(b) by 0 days.

(21) Appl. No.: 09/175,785

(22) Filed: Oct. 20, 1998

Related U.S. Application Data

(60) Provisional application No. 60/063,793, filed on Oct. 31, 1997.

(51) Int. Cl.[7] ............................. C07K 1/113; C12N 9/96
(52) U.S. Cl. .......................... 435/188; 530/322; 530/345; 530/391.5; 530/395; 530/409
(58) Field of Search ..................................... 530/322, 345, 530/391.5, 391.9, 395, 405, 409; 514/8; 435/188; 424/1.53, 1.69, 179.1, 180.1, 194.1, 94.3

(56) References Cited

U.S. PATENT DOCUMENTS

| | | | |
|---|---|---|---|
| 5,191,066 | * 3/1993 | Bieniarz et al. | 530/391.1 |
| 5,538,870 | 7/1996 | Noeth et al. | 435/91.2 |
| 5,538,872 | 7/1996 | Bahl et al. | 435/91.52 |
| 5,605,791 | 2/1997 | Ashkenazi et al. | 435/5 |
| 5,607,834 | 3/1997 | Bagwell | 435/6 |
| 5,824,805 | * 10/1998 | King et al. | 548/546 |

FOREIGN PATENT DOCUMENTS

85/05638 * 12/1985 (WO) .

OTHER PUBLICATIONS

Barbaric et al. Cross–linking, Stabilization and Detection . . . Acta Pharm. vol. 44, pp. 353–365, 1994.*

Heimgartner et al. Reversible and Irreversible Cross–linking . . . Biochem. J. vol. 267, pp. 585–591, 1990.*

Kozulic et al. Study of the Carbohydrate Part . . . Biochem. Biophys. Res. Comm. vol. 122, No. 3, pp. 1083–1090, Aug. 16, 1984.*

(List continued on next page.)

*Primary Examiner*—Jeffrey E. Russel
(74) *Attorney, Agent, or Firm*—Gibbons, Del Deo, Dolan, Griffinger & Vecchione

(57) ABSTRACT

The present invention describes a site specific conjugation method for glycoproteins wherein a stable dihydrazone bond is formed between the glycoproteins and the glycoproteins retain full activity. Also described is a novel glycoprotein-glycoprotein conjugate of the formula

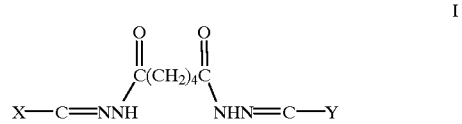

wherein X and Y are glycoproteins modified such that the vicinal hydroxyl groups of the carbohydrate moieties in the glycoproteins have been oxidized to aldehydes which are then reacted with a hydrazide functional group to form a hydrazone bond which is represented in Formula I by "—C=NNH—".

12 Claims, 2 Drawing Sheets

OTHER PUBLICATIONS

Kozulic et al. Preparation of the Stabilized Glycoenzymes . . . Appl. Biochem. Biotech. vol. 15, No. 3, pp. 265–278, Oct. 1987.*

Kralovec et al. Synthesis of Methotrexate–Antibody Conjugates . . . J. Med. Chem. vol. 32, No. 11, pp. 2426–2431, 1989.*

Hoffman, W.L. et al. "Site–specific immobilization of antibodies by their oligosaccharide moieties to new hydrazide derivatized solid supports", Journal of Immunological Methods, vol. 112, Mar. 1988, pp. 113–120.

O'Shannessy, D.J. et al. "Site–Directed Immobilization of Glycoproteins on Hydrazide–Containing Solid Supports", (Biotechnology and Applied Biochemistry), vol. 9, 488–496, 1987.

Melton, R.G. et al. "Antibody–directed enzyme prodrug therapy (ADEPT)", Drugs of the Future, 21(2): 167–181, 1996.

Nakane, P.K. et al. "Peroxidase–labeled Antibody: A New Method of Conjugation", The Journal of Histochemistry and Cytochemistry, vol. 22, No. 12, 1084–1091, Aug. 1974.

Wilson, M.B. et al. "Recent Developments in the Periodate Method of Conjugating Horseradish Peroxidase (HRPO) to Antibodies", *Immunofluorescence and Related Staining Techniques,* 215–224, 1978.

Chaplin, M.F. et al. *Carbohydrate Analysis: a Practical Approach,* Chapter 5 Glycoproteins; First Edition, 1986, p. 143.

Becker, W.M. *The World of the Cell,* Part Two Energy and the Cell, 1986, p. XV.

Stern, A.S. et al. "Increasing the Antigen Binding Capacity of Immobilized Antibodies", Dept. of Protein Biochemistry, Roche Research Center (not dated).

Ishikawa, E. et al. "Enzyme–Labeling of Antibodies", Journal of Immunoassay, vol. 4, Nov. 3, p. 209–211, 1983.

Tijssen, P. et al. "Highly Efficient and Simple Methods for the Preparation of Peroxidase and Active Peroxidase–Antibody Conjugates for Enzyme Immunoassays", Analytical Biochemistry, vol. 136, p. 451–457, 1984.

M. Imagawa, et al. "Characteristics and Evaluation of Antibody–Horseradish Peroxidase Conjugates Prepared by Using a Maleimide Compound, Glutaraldehyde, and Periodate", Journal of Applied Biochemistry, vol. 4, p. 41–57, 1982.

Carlsson, J. et al. "Protein Thiolation and Reversible Protein–Protein Conjugation", Biochem. J., vol. 173, p. 723–737, 1978.

Genzyme, Genzyme Research Products Catalog, Growth Factors, p. 138–146 (not dated).

Avrameas, S. "Coupling of Enzymes to Proteins with Gluteraldehyde. Use of the Conjugates for the Detection of Antigens and Antibodies", Immunochemistry, vol. 6, p. 43–52, 1969.

Avrameas, S. et al. "The Cross–Linking of Proteins With Glutaraldehyde and Its Use for the Preparation of Immunoabsorbents," Immunochemistry, vol. 6, p. 53–66, 1969.

Avrameas, S. et al. "Communications to the Editors: Peroxidase labelled antibody and Fab conjugates with enhanced intracellular penetration", Immunochemistry, vol. 8, p. 1175–1179, 1971.

Clyne, D.H. et al. "Antibody Enzyme Conjugates: The Preparation of Intermolecular Conjugates of Horseradish Peroxidase and Antibody and their Use in Immunohistology of Renal Cortex", The Journal of Histochemistry and Cytochemistry, vol. 21, No. 3, p. 233–240, 1973.

Myers, D.E. et al. "The effects of aromatic and aliphatic maleimide crosslinkers on anti–CD5 ricin immunotoxins", Journal of Immunological Methods, vol. 121, p. 129–142, 1989.

Welinder, K.G. et al. "Amino Acid Sequence Studies of Horseradish Peroxidase. I. Tryptic Peptides", Canadian Journal of Biochemistry, vol. 50, 1972, pp. 44–62.

Zara, J.J. et al. "A Carbohydrate–Directed Heterobifunctional Cross–Linking Reagent for the Synthesis of Immunoconjugates", Analytical Biochemistry, vol. 194, p. 156–162, 1991.

Avigad, G. et al. "The D–Galactose Oxidase of *Polyporus circinatus*", The Journal of Biological Chemistry, vol. 237, No. 9, 1962, pp. 2736–2743.

Van Lenten, L.V. et al. "Studies on the Chemical and Enzymatic Modification of Glycoproteins", The Journal of Biological Chemistry, vol. 246, No. 6, 1971, pp. 1889–1894.

Kerr, D.E. et al. "Regressions and cures of melanoma xenografts following treatment with monoclonal antibody beta–lactamase conjugates in combination with anticancer prodrugs", Cancer Res, vol. 55(16), p. 3558–3563, 1995. (Abstract only).

Yoshitake, S. et al. "Conjugation of Glucose Oxidase from *Aspergillus niger* and Rabbit Antibodies Using N–Hysdroxysuccinimide Ester of N–(4–Carboxycyclohexylmethyl)–Maleimide", Eur. J. Biochem, vol. 101, p. 395–399, 1979.

R. Wei, et al. "Preparation of a Phospholipase C–Antihuman IgG Conjugate, and Inhibition of Its Enzymatic Activity by Human IgG", Clin. Chem. 23/8, p. 1386–1388, 1977.

Genzyme Research Products Catalog, Genzyme Interleukin–4, p. 55–57. (Not dated).

Jeanson, A. et al. "Preparation of Reproducible Alkaline Phospatase–Antibody Conjugates for Enzyme Immunoassay Using a Heterobifunctional Linking Agent", vol. 172, p. 392–396, Analytical Biochemistry, 1988.

Ford, D.J. et al. "Characterization of Glutaraldehyde Coupled Alkaline Phosphatase–Antibody and Lactoperoxidase–Antibody Conjugates", Immunochemistry, vol. 15, p. 237–243, 1978.

Means, G.E. et al. "Chemical Modifications of Proteins: History and Applications", Bioconjugate Chem., vol. 1, No. 1, p. 2–12, 1990.

Wong, S.S. "Chemistry of Protein Conjugation and Cross Linking", CRC, Boca Raton, 75–189, 1985.

Cumber, A.J. et al., "Preparation of Antibody–Toxin Conjugates", Meth. Enzymol., 112, 207–225. 1985.

Kawaoi, A. and Nakane, P.K., "Federal Proceedings", Fed. Proc. 32, 840, 1972.

Ege, S.N. *Organic Chemistry,* Chapter 13, p. 504, D.C. Heath and Company, Lexington, MA, 1989.

* cited by examiner

SITE-SPECIFIC CONJUGATION OF GLYCOPROTEINS

This application claims priority under 35 U.S.C. §119(e) of provisional application Ser. No. 60/063,793, filed Oct. 31, 1997.

BACKGROUND OF THE INVENTION

Enzyme-antibody conjugates are among the most important reagents in biomedical/biochemical research and applications. Numerous reagents and methods for coupling enzymes to antibody molecules (mostly IgG) have been developed. Most of these coupling methods involve the use of cross linking reagents such as homobifunctional cross-linkers, or heterobifunctional cross linking reagents (Wong, S. S., *Chemistry of Protein Conjugation and Cross-Linking*, CRC, Boca Raton, 75–189 (1991); Ishikawa, E., et. al., *Journal of Immunoassay* 4(3), 209–327 (1983); Means, G. E. and Feeney, R. E., *Bioconjugate Chem.* 1, 2–12 (1990)). Most protein cross-linking chemistries are conducted either through lysine (Lys) residues which contain primary amines, aspartic acid (Asp) or glutamic acid (Glu) residues which contain carboxyl groups, or cysteine (Cys) residues which contain sulfhydryl groups. However, Lys, Asp, Glu, and Cys are among the six most frequently appearing amino acid residues in the active sites of proteins (e.g., enzymes) (Becker, W. M., *World of the Cell*, Benjamin Cummings, Menlo Park, Calif., 147–174 (1986)). In addition, in most cases, the coupling of proteins through cysteines or lysines is not site-specific due to the random distribution of these residues in protein molecules. Consequently, crosslinking enzymes and antibodies through these residues may result in cross-linking at or near the active sites of these molecules impairing the biochemical functions (e.g., the catalytic activity of enzymes, the antigenic binding affinity of antibodies) of the conjugated protein molecules due to the blocking of the active site.

Glutaraldehyde is a typical homobifunctional cross-linking reagent and has long been used to prepare enzyme-antibody conjugates (Avrameas, S., *Immunochemistry* 6, 43–52 (1969); Avrameas, S. and Ternynck, T., *Immunochemistry*, 6, 53–66 (1969)). Glutaraldehyde cross-links proteins by forming a Schiff's base between two aldehyde groups and two lysine residues, one from each of the protein molecules. The disadvantage of this method is that self-conjugation of the protein molecules may occur. Methods which reduce protein self-conjugation may also lead to over polymerization in which three or more protein molecules crosslink to each other due to the excess number of derivatized groups on the proteins (Avrameas, S. and Ternynck, T., *Immunochemistry* 8, 1175–9 (1971); Clyne, D. H., et. al., *J. Histochem. Cytochem.* 21, 233–40 (1973)).

Conjugating proteins utilizing heterobifunctional reagents as crosslinkers, which usually involves the labeling of one or both proteins with the cross-linkers, eliminates the problem of self-coupling between molecules of the same protein. In a very common conjugation method, enzyme molecules are first labeled with a NHS-ester-maleimide heterobifunctional reagent (Yoshitake, S., et al., *Eur. J. Biochem.* 101–395 (1979); Myers, D. E., et al. *J. Immunol. Meth.* 121, 129–142 (1989)). IgG has been labeled with a NHS-pyridyldithiol cross-linker (Carlsson, J., et al., *J. Biochem.* 173, 723–737 (1978); Cumber, A. J., et al., *Meth. Enymol.* 112, 207–225 (1985)) which is then reduced to generate free sulfhydryl groups (—SH). The antibody molecules are conjugated to the enzyme molecules through the nucleophilic addition of the —SH groups to the maleimide groups on the enzyme. However, a disadvantage of using heterobifunctional crosslinking reagents is that the site of crosslinking on the proteins is nonspecific and may result in the loss of activity of the proteins.

Glycoproteins can be cross-linked through their carbohydrate moieties. The oligosaccharide moieties of glycoproteins are often located at sites far away from the active or binding sites of the proteins and therefore are not usually involved in binding to ligands. This was demonstrated in IgG where the IgG was crosslinked through the carbohydrate groups, located on the complement fragment (Fc) region. The antigen binding fragment (Fab) of the IgG bound to the antigen almost as well as the intact IgG; (Avrameas, S. and Ternynck, T., *Immunochemistry* 8, 1175–9 (1971)). Results of studies of enzyme mechanisms suggest that carbohydrate moieties are not involved in the binding of the enzymes to their substrates (Becker, W. M., supra).

Enzyme-antibody conjugates joined through carbohydrate groups have been prepared by converting the vicinal hydroxyl groups of the carbohydrate moieties to aldehydes via periodate oxidation (Kawaoi, A. and Nakane, P. K., *Fed. Proc.* 32, 840 (1972)). The conjugation of horseradish peroxidase (BRP) to IgG has been described, wherein the aldehyde groups generated on HRP reacted with the primary amines on IgG to form Schiff's bases, which were subsequently stabilized through reduction by sodium borohydride. This method, however, resulted in self-coupling of the enzyme molecules and subsequent blocking of the active site on the enzyme. Amino-blocking reagents, such as 1-fluoro-2,4-dinitrobenzene, which react with reactive lysine residues, have been used to prevent self-coupling of HRP-aldehyde (Nakane, P. K. and Kawaoi, A., *J. Histochem. Cytochem.* 22, 1084–1091 (1974); Wilson, M. B. and Nakane, P. K., *Immunofluorescence and Related Staining Techniques*, Elsevier, Amsterdam, 215–224 (1978); Imagawa, M., et. al., *J. Applied Biochem.* 4, 41–57 (1982); Tijssen, P. and Kurstak, E., *Anal. Biochem.* 136, 451–7 (1984)). However, the use of amino-blocking reagents has limited applicability since lysine residues are crucial for maintaining ligand-binding activity among many proteins. Therefore, conjugation chemistry involving the formation of Schiff's bases still presents the disadvantage of blocking enzyme active sites and antibody binding sites.

Hydrazide, hydrazine, or semicarbazide containing compounds, which modify aldehydes generated on glycoproteins through the formation of a stable hydrazone bond between the aldehyde and hydrazide, have been used in an attempt to overcome the various difficulties encountered in Schiff's base chemistry. This methodology has been used to immobilize IgG to a solid matrix. The IgG molecules immobilized through their carbohydrate moieties to hydrazide-containing agarose beads displayed an enhanced antigenic affinity about three times higher than IgG molecules immobilized through lysine residues. (O'Shannessy, D. J. and Hoffman, W. L., *Biotechnol. Appl. Biochem.* 9, 488–496 (1987); Hoffman, W. L. and O'Shannessy, D. J., *J. Immunol. Method,* 112, 113–120 (1988)). A heterobifunctional cross-linking reagent containing a hydrazide group and a pyridyl disulfide moiety was used for coupling antibodies to molecules containing a free sulfhydryl group, wherein the modified antibodies retained full antigen binding ability (Zara, J. J. et. al., *Anal. Biochem.* 194, 156–162 (1991)). A method of crossinking a glycoprotein to a protein containing free sulfhydryl groups using a cross-linking reagent which combines a nucleophilic hydrazide residue with an electrophilic maleimide residue has been described. (U.S. Pat. No. 5,605,791). These two methods, however, require the presence of a free sulfhydryl group on one of the proteins to be conjugated and these conjugation methods may block the active site of one of the proteins.

Therefore, it is an object of the present invention to provide a method of conjugating proteins which not only eliminates protein self-coupling but also provides for optimum orientation of the active sites of the conjugated proteins and minimizes blocking of active sites such that the proteins retain full biological activity.

SUMMARY OF THE INVENTION

In one aspect, the invention concerns a method for the site-specific covalent conjugation of two or more glycoproteins through their carbohydrate residues, comprising: (a) mixing a first oxidized glycoprotein with a dihydrazide or dihydrazine containing reagent to form a glycoprotein-hydrazide or glycoprotein-hydrazine intermediate, wherein a hydrazone bond is formed between the aldehyde group of the first glycoprotein and a hydrazide or hydrazine group of the dihydrazide or dihydrazine reagent; and (b) mixing a second oxidized glycoprotein with the glycoprotein-hydrazide or glycoprotein-hydrazine intermediate of step (a) to form a second hydrazone bond between the aldehyde of the second oxidized glycoprotein and the other unreacted hydrazide or hydrazine of the dihydrazide or dihydrazine reagent, generating a glycoprotein-glycoprotein conjugate. Both glycoproteins in the glycoprotein-glycoprotein conjugate retain their full independent biological activity.

In a further aspect, the invention provides a method for the covalent conjugation of an enzyme and antibody through their carbohydrate residues. In a preferred embodiment, alkaline phosphatase (ALP) and IgG are oxidized by sodium periodate to generate aldehyde groups on both proteins. IgG-aldehyde is reacted with a 5–500,000 molar excess over the amount of protein of adipic dihydrazide to generate a hydrazone bond between the aldehyde group and one hydrazide functional group of the adipic dihydrazide molecule, while the other hydrazide functional group on the dihydrazide remains free. After removing the excess unreacted adipic dihydrazide reagent, the IgG-hydrazide is reacted with ALP-aldehyde and is conjugated to the ALP molecule through the formation of a second hydrazone bond between the aldehyde on the ALP and the free hydrazide functional group. After conjugation, the binding/active sites on both the IgG and ALP are free to interact with their respective ligand or substrate.

In still a further aspect, the invention concerns a glycoprotein-glycoprotein conjugate of the formula

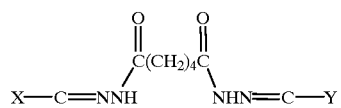

wherein X and Y are glycoproteins modified such that the vicinal hydroxyl groups of the carbohydrate moieties in the glycoproteins have been oxidized to aldehydes which are then reacted with a hydrazide functional group to form a hydrazone bond which is represented in Formula I by "—C=NNH—".

The vicinal hydroxyl groups of the carbohydrate residue are represented by

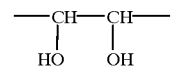

Figure 2:
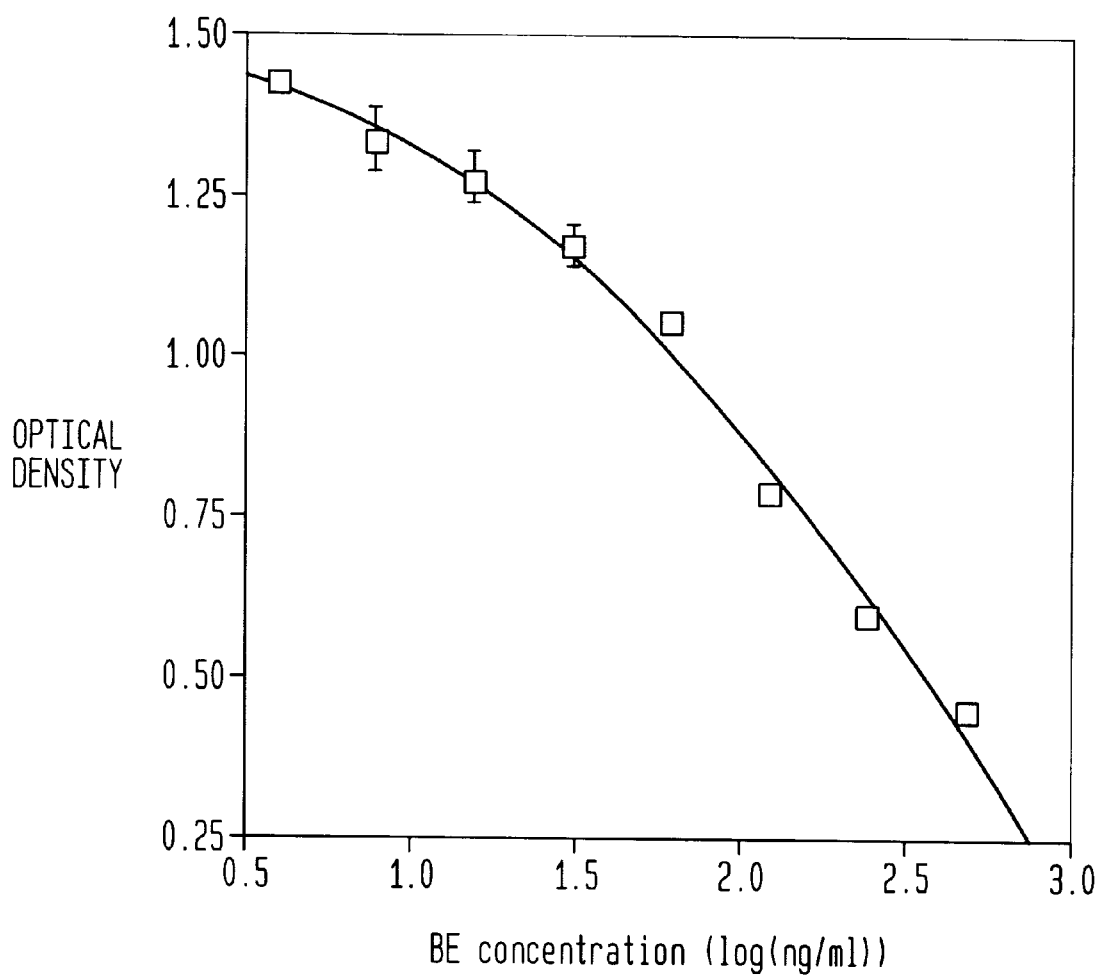

FIG. 2 illustrates the results of a microtiter plate based ELISA for benzoylecgonine (BE) using the ALP-anti-BE IgG conjugate prepared according to the method of the present invention.

DETAILED DESCRIPTION OF THE INVENTION

The present invention provides a novel method for the covalent conjugation of glycoprotein molecules by a coupling of the glycoproteins through the use of a dihydrazide or dihydrazine containing reagent that holds the proteins in such a position as to allow the formation of a hydrazone bond between the hydrazide or hydrazine functionality of the dihydrazide or dihydrazine containing reagent and an aldehyde group generated via periodate oxidation on a carbohydrate residue of each glycoprotein.

The present invention provides a novel method for the site specific covalent conjugation of two or more glycoprotein molecules through their carbohydrate moieties. In one embodiment, the present invention provides a method for the site specific conjugation of two or more glycoproteins through the carbohydrate residues on the glycoproteins, comprising (a) contacting a first glycoprotein with an oxidizing reagent, the reagent being present in the mixture in an amount which is greater than a 1:1 molar ratio to the molar amount of the glycoprotein present, to form an aldehyde group on the first glycoprotein; (b) removing excess unreacted oxidizing reagent from the reaction mixture of step (a); (c) contacting the first glycoprotein of step (b) with a dihydrazide or dihydrazine containing reagent, the reagent present in the reaction mixture in a molar amount in excess over the molar amount of oxidized glycoprotein present, to form a hydrazone bond between the aldehyde group on the glycoprotein and a first hydrazide or hydrazine on the dihydrazide or dihydrazine reagent, thereby generating a first glycoprotein-hydrazide or glycoprotein-hydrazine conjugate; (d) removing excess unreacted hydrazide or hydrazine reagent from the mixture of step (c); (e) contacting a second glycoprotein with an oxidizing reagent, the reagent present in the mixture in a greater than 1:1 ratio molar amount to the molar amount of glycoprotein present, to generate an aldehyde on the second glycoprotein; (f) removing excess unreacted oxidizing reagent from the mixture of step (e); and (g) contacting the glycoprotein-hydrazide or glycoprotein-hydrazine conjugate of step (d) with the second glycoprotein of step (f) to form a second hydrazone bond between the aldehyde on the second glycoprotein and the unreacted hydrazide or hydrazine of the dihydrazide or hydrazine reagent, thereby generating a glycoprotein-glycoprotein conjugate.

The term "glycoprotein" refers to any polypeptide containing one or more carbohydrate residues or moieties. The term "carbohydrate" can include but is not limited to a monosaccharide or oligosaccharide having one or any combination of the following monosaccharides: fucose, galactose, N-acetylgalactosamine, glucose, N-acetylglucosamine, mannose and N-acetylneuraminidate.

This novel method results in the formation of a novel chemical entity which possesses the characteristic biochemical and/or biological properties and activities of each of the single starting protein molecules which comprise this cluster. The novel chemical structure has the formula

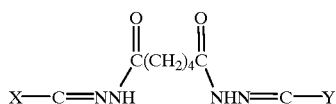

wherein X and Y are glycoproteins modified such that the vicinal hydroxyl groups of the carbohydrate moieties in the glycoproteins have been oxidized to aldehydes which are then reacted with a hydrazide functional group to form a hydrazone bond which is represented in Formula I by "—C=NNH—".

The novel conjugation chemistry of the present invention for site-specific cross-linking of glycoproteins has a wide range of applicability since greater than 90% of proteins are glycoproteins (*Carbohydrate Analysis, a Practical Approach*, Chaplin, M. F. and Kennedy, J. F. (eds)). IRL Press, Washington, D. C., 143 (1986)). The novel method of the present invention can be used to prepare enzyme-IgG conjugates for enzyme immunoassays of different format, for example, sandwich type enzyme immunoassays and competitive enzyme immunoassays. The method of the present invention can be used for antibody-directed enzyme prodrug therapy (ADEPT) wherein antibody-enzyme conjugates are directed at tumor-associated antigens to achieve site-specific activation of prodrugs to potently cytotoxic species maintaining both enzyme activity and antibody binding activity (Melton, R G., et al., *Drugs of the Future* 21, 167–181 (1996)). The novel conjugation chemistry of the present invention can also be used to cross-link glycoprotein receptor (target) molecules to enzymes for various biochemical and biomedical research applications (Genzyme Research Products Catalog pgs. 55–57), for example, in biosensors. The method of the present invention can also be used to conjugate oligonucleotides (DNA or RNA molecules) to enzymes for DNA detection through the oxidation of the ribose unit on the nucleotide backbone by periodate.

The glycoproteins to be conjugated using the method of the present invention will preferably be in purified form. Enzymes to be used in the method of the present invention include any enzyme that contains one or more carbohydrate moieties. The method of the present invention is applicable to any antibody.

More specifically, the present invention involves the oxidation of the carbohydrate moieties on proteins to be conjugated to form aldehyde groups. Aldehyde groups can be generated from the carbohydrate moieties on a glycoprotein either enzymatically, e.g. using galactose oxidase (Avigad, E., et al., *J. Biol. Chem.* 237, 2736–42 (1962), or chemically, e.g. using periodate. Sodium periodate oxidizes the vicinal hydroxyls of carbohydrates (Van Lenten, L. and Ashwell, G., *J. Biol. Chem.* 246, 1889–94 (1971)). It has been found for purposes of the present invention that using sodium periodate as an oxidizing agent in an amount that is in molar excess over the amount of glycoprotein to be oxidized provides the most desirable results such that the glycoproteins retain full biological activity after oxidation. A concentration range of from about 0.01–500 mM of sodium periodate is preferred; a concentration of 10 mM is most preferred. Protein concentration can be in the range of from about 0.01 mg/ml to about 100 mg/ml, preferably 5 mg/ml. The reaction time for oxidation can be from about 1 minute to 2 hours depending upon the pH of the reaction mixture and the concentration of $NaIO_4$. In a preferred embodiment, the oxidation reaction time was 30 minutes. After oxidation is complete, excess sodium periodate should be removed by, for example, desalting, dialyzing or reacting the oxidation mixture with alcohols containing vicinal hydroxy groups and then desalting and dialyzing.

The next step of the novel method of the invention is reacting the aldehyde groups formed on the glycoproteins with a large excess of a dihydrazide or dihydrazine containing molecule to form a hydrazone bond between the aldehydes and one of the hydrazide or hydrazine functionalities of the dihydrazide or dihydrazine containing molecule. Any compound containing two or more hydrazide or hydrazine groups may be successfully used as the cross-linker in preparing site-specific glycoprotein conjugates according to the present invention. Such compounds include, but are not limited to, adipic dihydrazide, succinic dihydrazide, and 1,6-hexyldihydrazine. The amount of dihydrazide or dihydrazine compound that can be reacted with a glycoprotein molecule is in the range of from about 5–500,000 molar ratio of dihydrazide or dihydrazine over glycoprotein. Preferably the molar range of the dihydrazide or dihydrazine compound used is 100–20,000 times the molar ratio of protein present. The time of reaction is not critical, however, the preferred reaction time is at least about 5 minutes. Excess dihydrazide or dihydrazine containing reagent should be removed from the reaction after it is complete via desalting or dialyzing. The modified glycoproteins, that is the hydrazone containing glycoprotein and the other glycoprotein containing an aldehyde, are then mixed until the desired conjugation takes place between the aldehyde and second hydrazide or hydrazine functionality and a second hydrazone bond is formed. The time of this coupling reaction is from about 30 minutes to about 18 hours depending on the temperature at which the reaction takes place, which can be from about 4° C. to room temperature.

It has been found in the present invention that the periodate oxidation of the glycoprotein carbohydrate residues to aldehydes, as well as the adipic dihydrazide labeling of the oxidized glycoproteins, carried out at slightly acidic pH (pH 5.5) successfully overcame the problem of self-coupling found in other conjugation methods. Non-specific coupling occurs in other methods involving periodate oxidation and Schiff's base formation, wherein an imine bond forms between the newly generated aldehyde and a lysine residue on one of the protein molecules. This reaction proceeds optimally at slightly basic conditions and the formation of an imine bond is a highly reversible reaction. In contrast, the formation of a hydrazone bond between a hydrazide and an aldehyde is catalyzed by acid, and the preferred pH for this reaction is around pH 5.0, most preferably at pH 5.5 (Ege, S. N., *Organic Chemistry*, Chapter 13, page 504, D. C. Heath and Company, Lexington, Mass. (1989)). A hydrazide group has a pKb of ~3.0 (Shearwater Polymers, Inc., *Polyethylene Glycol Derivatives* (Catalog), "PEG-Hydrazide Hydrochloride", p. 11 (January 1996)) and at a pH of 5.5, the majority of hydrazide is deprotonated. At pH 5.5, less than one out of $10^4$ lysine residues on the proteins is in deprotonated form. Even if a small number of imine bonds were formed during protein oxidation and desalting, the introduction of hydrazide groups would convert almost all of the imine bonds to the much more stable hydrazone bonds. Therefore, the method of the present invention minimizes non-specific coupling and provides a stable linkage between the molecules.

Optionally, the unreacted aldehydes and/or unreacted hydrazides/hydrazines remaining after the final coupling step can be blocked. Molecules containing one or more hydrazide/hydrazine groups, preferably one, can be used to block unreacted aldehyde groups. To block unreacted hydrazide/hydrazine groups, molecules containing one or more aldehyde groups, preferably one, such as formaldehyde, can be used.

The method of the present invention produces a glycoprotein conjugate of the formula

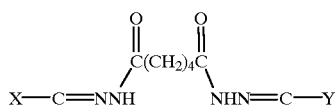

I wherein X and Y are glycoproteins modified such that the vicinal hydroxyl groups of the carbohydrate moieties in the glycoproteins have been oxidized to aldehydes which are then reacted with a hydrazide functional group to form a hydrazone bond which is represented in Formula I by "—C=NNH—". The two hydrazone bonds joining the protein molecules are stable bonds and are generated using mild reaction conditions that allow the glycoprotein molecules X and Y to retain virtually full biological activity.

In a preferred embodiment of the present invention, an anti-benzoylecgonine (anti-BE) IgG-alkaline phosphatase conjugate was prepared. Alkaline phosphatase (ALP) and IgG were independently reacted with 10 mM $NaIO_4$ for 30 minutes at pH 5.5 to generate aldehyde groups on the carbohydrate residues on each of the glycoproteins. It was found that after oxidation the ALP retained full activity.

The oxidized ALP and IgG molecules, ALP—CHO and IgG—CHO, respectively, were coupled using adipic hydrazide as the coupling agent through the formation of two hydrazone bonds: one hydrazone bond was formed between a hydrazide group of the adipic dihydrazide molecule and the aldehyde of the IgG, and the other hydrazone bond was formed between the aldehyde of the ALP and the second unreacted hydrazide group on the same adipic dihydrazide molecule. It was found that using a ten-thousand-fold molar excess of adipic dihydrazide over the amount of IgG greatly favored the reaction of one aldehyde group on the IgG per adipic dihydrazide molecule and significantly reduced self-coupling of IgG molecules. Each aldehyde group was derivatized by one adipic dihydrazide molecule, leaving the second reactive hydrazide functional group of the dihydrazide intact for conjugating to an aldehyde group on ALP.

Figure 1:
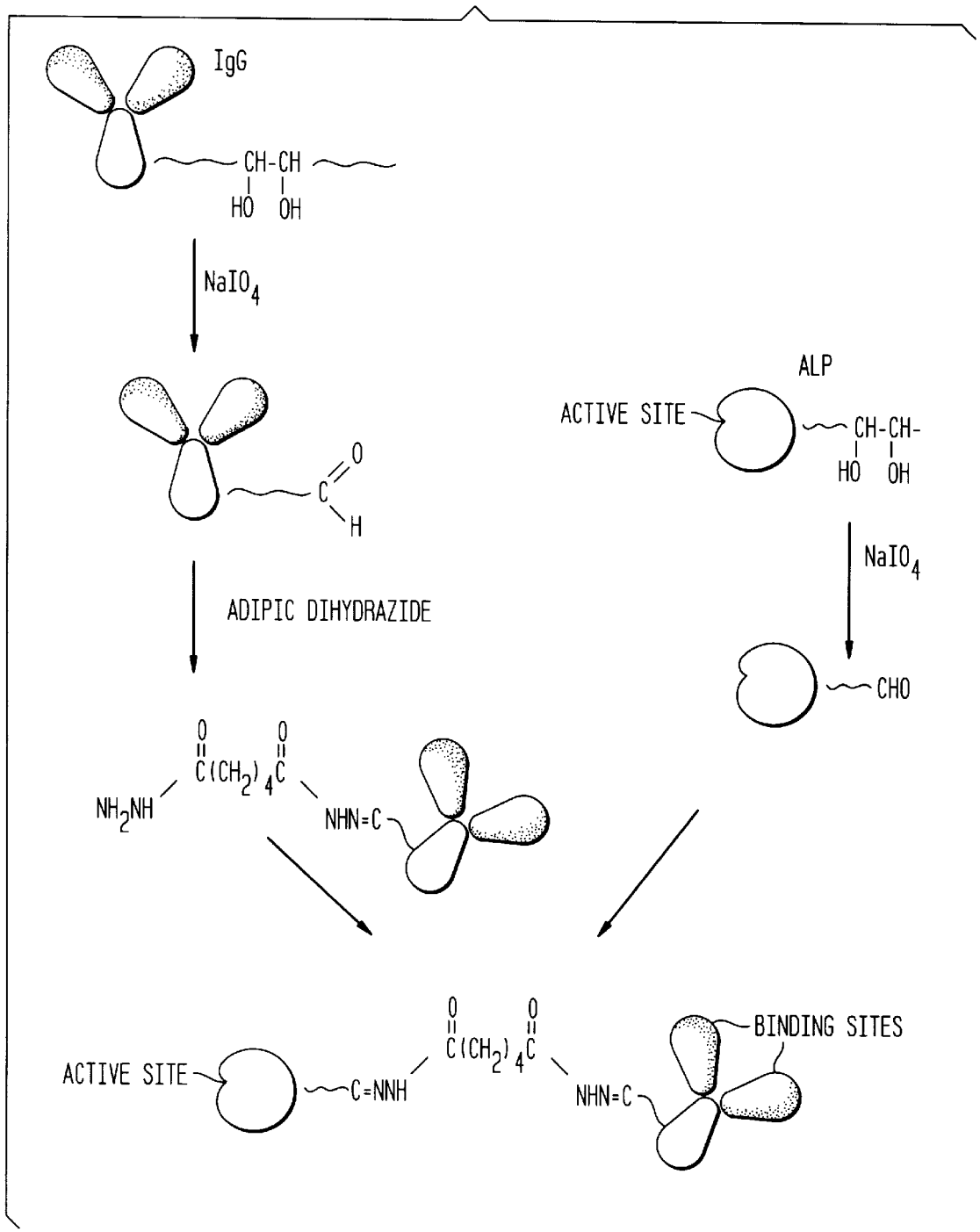
FIG. 1 illustrates the conjugation of antibody (IgG) to enzyme (ALP) as follows: (a) oxidation of the vicinal hydroxyl groups of the carbohydrate residue of the antibody with NaIO$_4$ to generate an aldehyde; (b) oxidation of the vicinal hydroxyl groups of the carbohydrate residue of the enzyme with NaIO$_4$ to generate an aldehyde; (c) reaction of the antibody-aldehyde with a dihydrazide containing reagent attaching the reagent to the antibody via a hydrazone bond; (d) attachment of the aldehyde-enzyme to the available hydrazide functionality via a second hydrazone bond to form the complete conjugate.

The hydrazide labeled IgG then reacted with ALP—CHO to form the IgG—ALP conjugate. Both the enzyme and the antibody in the conjugate are positioned such that their active sites can fully react with their respective ligand/substrate. FIG. 1 illustrates the chemical reactions involved in conjugating IgG to ALP.

It will be appreciated that the dihydrazide or dihydrazine reagent can be first reacted with either of the oxidized glycoproteins to be conjugated. The reagent can first be reacted with the oxidized enzyme or oxidized antibody and the obtained intermediate can be further reacted with the other oxidized glycoprotein.

The novel method of the present invention results in an antibody-enzyme conjugate that retains excellent enzyme and antibody activities. FIG. 2 illustrates the results of an ELISA for BE using the ALP-anti-BE IgG conjugate as prepared above. The competitive assay showed good binding and inhibition properties of the antibody using the conjugation conditions described herein.

The results shown herein confirmed that both the enzyme and antibody protein molecules retained optimum orientation of binding sites on both molecules.

There is great flexibility in the method of conjugation and conditions will largely depend on convenience, materials available, temperature, time and protein concentration.

Based on the information provided herein, the design of a conjugation method for the preparation of any glycoprotein-glycoprotein conjugate is well within the knowledge of a person skilled in the art.

While this invention has been described in connection with specific embodiments thereof, it will be understood that one of skill in the art can adapt the essential features of the invention to various usages and conditions as come within known or customary practice within the art to which the invention pertains without departing from the spirit and scope thereof.

EXAMPLES

Apparatus and Reagents. UV-Vis absorbance was measured on a Beckman DU-70 spectrophotometer. Microtiter plates were read on a Titertek Multiscan Plus plate reader. Mouse anti-benzoylecgonine (anti-BE) antibodies were produced and purified in-house (Roche product # BE 262.2). Alkaline phosphatase was obtained from Sigma (Saint Louis, Mo.). BE-BSA (product # PD 1) conjugate and benzoylecgonine (BE) (product Lot # 26897-222-03286) were production stock of OnTrak TesTcup® BE assay. Adipic dihydrazide and sodium periodate were obtained from Aldrich (Milwaukee, Wis.). Fluorescein thiosemicarbazide (FTSC) was obtained from Molecular Probes, Inc. (Eugene, Oreg.). All other chemicals were reagent grade.

Example 1

Measurements of ALP Activity After Periodate Oxidation 2.0 ml of 1.0 mg/ml ALP was prepared by desalting alkaline phosphatase stock solution using Econo-Pac 10DG desalting columns from Bio-Rad (Hercules, Calif.) according to manufacturer's instructions using NaAc buffer (0.1M NaAc, 0.15M NaCl, pH 5.5/0.02% $NaN_3$) as the eluting buffer. 0.2 ml of the desalted 1.0 mg/ml ALP solution was aliquoted into each of 10 tubes. 22 $\mu$l of distilled water was added to each of two tubes which served as controls. To each of the remaining 8 tubes was added 22 $\mu$l of 0.1M $NaIO_4$ (in water) to obtain a final periodate concentration of 10 mM per tube. After mixing, the tubes with $NaIO_4$ were incubated in the dark. After 10 minutes incubation, 40 $\mu$l of 50% ethylene glycol was added to two of the tubes to stop the reaction. Similarly, the reactions in another two tubes were stopped after 20 minutes, 30 minutes and 40 minutes incubation with $NaIO_4$. Finally, 40 $\mu$l of 50% ethylene glycol was added to each of the two control tubes. 10 $\mu$l of solution was taken out of each tube and diluted to 4.0 ml with sodium borate buffer (0.1 M $Na_2B_4O_7$, pH 8.75). To test the enzyme activity with a substrate, 10 $\mu$l of each of the diluted ALP solutions was added to the wells, in quadruplicate, of a microtiter plate and incubated with 50 μl of p-nitrophenol phosphate (p-NPP: 2.0 mg/ml in 1.0M diethanolamine, pH 9.8) for 3 minutes, after which the reaction was stopped by adding 50 μl of 3N NaOH to each well. The plate was read at 405 nm. Table 1 illustrates ALP activity after exposure to 10 mM $NaIO_4$ for 0, 10, 20, 30 and 40 minutes. Relative ALP activity was determined as follows: the optical density (O.D.) generated by ALP at 0 minutes was taken as 100%. The O.D. reading of the enzyme in the other time point sets was compared to the control to calculate relative ALP activity.

TABLE 1

Effect of $NaIO_4$ oxidation on the enzymatic activity of ALP and the number of aldehyde groups generated from the carbohydrate (—CHO) moieties of ALP.

| oxidation time (minutes) | number of —CHO generated[2] | relative ALP activity (%) a ± δ[3] |
|---|---|---|
| 0[1] | 0 | 100 ± 5 |
| 10 | 1.1 | 103 ± 4 |
| 20 | 1.1 | 102 ± 5 |
| 30 | 2.0 | 106 ± 6 |
| 40 | 2.0 | 107 ± 16 |

[1]Oxidation time 0: no $NaIO_4$ added to ALP solution.
[2]Number of —CHO groups on an ALP molecule which reacted with FTSC. Each value represents the average of two parallel experiments.
[3]Each value "a" represents an average of eight measurements from two parallel experiments of ± "δ" standard deviation.

The data in Table 1 demonstrate that no significant change of enzyme activity occurred. ALP demonstrated its ability to catalyze the conversion of p-nitrophenyl phosphate to p-nitrophenol and retained full activity after up to 40 minutes reaction time with $NaIO_4$.

Example 2

Determination of the Number of Aldehyde Groups Generated on ALP

The remaining ALP solution in each of the 10 tubes from Example 1 was individually desalted through a 10 DG column and eluted with NaAc buffer according to manufacturer's instructions. 0.5 ml fractions were collected and those containing the highest concentration of protein (by $OD_{278}$) were pooled (3 fractions in each case). Fifty μl of 0.5 mg/ml FTSC was added to each of the 10 pooled ALP solutions and the solutions were incubated for 2 hours at RT. Scheme I below illustrates the reaction between FTSC and an aldehyde group "ALP—CHO" or "IgG—CHO". The solutions were desalted as above, and 1.0 ml fractions were collected. Fractions # 4, 5, and 6 were pooled in each case and concentrated to 0.5 ml using an Amicon microconcentrator with a 30 KD M.W. cutoff. The absorbance of the concentrated ALP-FTSC solution was scanned from 230 to 700 nm.

The number of aldehyde groups generated on the oxidized glycoprotein which were available for conjugating one glycoprotein to another using the method of the present invention was determined by reacting the aldehyde groups with FTSC. FTSC reacts with free aldehyde groups to form hydrazone bonds. The glycoprotein and FTSC absorbing peaks were measured and the molar ratio of FTSC/glycoprotein was calculated for the FTSC labeled glycoprotein. A comparison of the spectroscopy of FTSC alone and of FTSC conjugated to the oxidized glycoprotein indicated that conjugation of FTSC to the oxidized glycoprotein did not significantly affect the optical behavior of either the oxidized glycoprotein or the FTSC molecule.

Two aldehyde groups were generated per ALP molecule after 30 minutes reaction time with $NaIO_4$, as determined by detection of the amount of FTSC conjugated to ALP (See Table 1) and were therefore available for reaction with another glycoprotein.

SCHEME 1

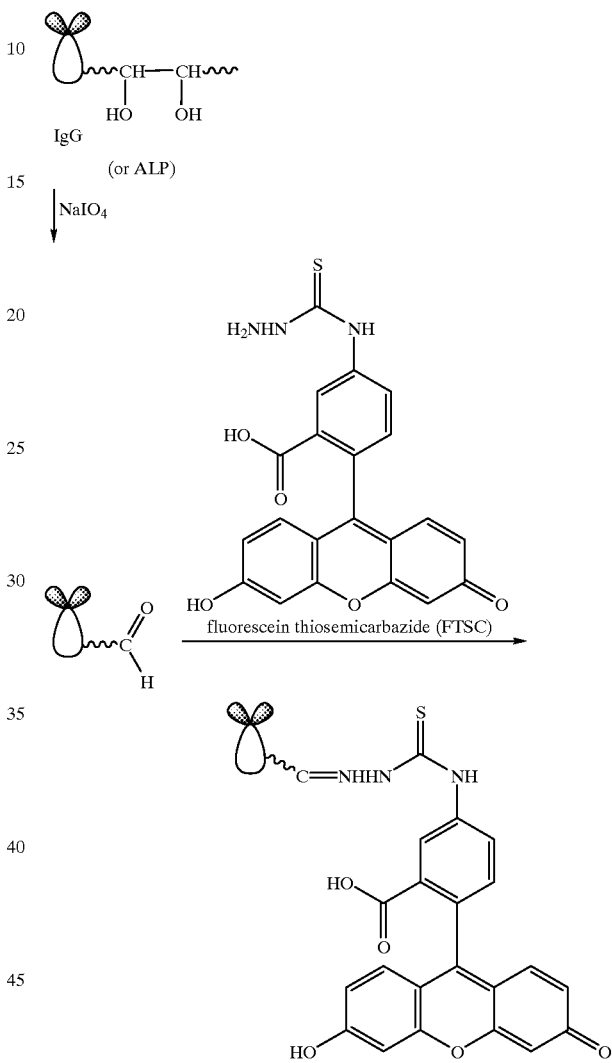

Example 3

Effect of Time of Periodate Oxidation on the Number of Aldehyde Groups Generated on IgG Five ml of 1.0 mg/ml monoclonal anti-BE IgG (in NaAc buffer) was aliquoted into each of ten tubes, each containing 0.5 ml IgG solution. 21 μl of distilled water was added to two of the tubes and served as controls. To each of the remaining 8 tubes was added 21 μl of 0.25M $NaIO_4$ (in distilled water) for a final concentration of 10 mM $NaIO_4$ in each tube. All ten tubes were kept away from light. After 10 minutes incubation with $NaIO_4$, 100 μl of 50% ethylene glycol was added to two of the tubes to stop the reaction. Similarly, the reactions in another two tubes were stopped after 20 minutes, 30 minutes, and 40 minutes incubation with $NaIO_4$. Finally, 100 μl of 50% ethylene glycol was added to each of the two control tubes. Each tube was then individually desalted through a 10 DG column eluted with NaAc buffer according to manufacturer's instructions and 1.0 ml fractions were collected. The fractions containing the highest concentration of protein were incubated with 50 µl of 0.5 mg/ml FTSC for 2 hours at RT. The solutions were desalted as above, and 1.0 ml fractions were collected. The absorbances of the fractions containing the most protein (as determined by $OD_{278}$) were scanned from 230 to 700 nm. Scheme I illustrates the $NaIO_4$ oxidation of IgG and the subsequent reaction of the aldehyde group generated with using FTSC.

Table 2 shows the time course of oxidation of IgG with $NaIO_4$ and the number of aldehyde groups generated from each IgG molecule as quantitated using FTSC. An average of 1.7 aldehydes were generated during the oxidation reaction.

TABLE 2

Time course of oxidation of IgG by $NaIO_4$

| oxidation time | number of —CHO groups generated[2] |
|---|---|
| 0[1] | 0 |
| 10 minutes | 1.3 |
| 20 minutes | 1.5 |
| 30 minutes | 1.7 |
| 40 minutes | 1.7 |

[1]Oxidation time 0: no $NaIO_4$ added to IgG solution.
[2]Number of —CHO groups on an average IgG molecule which were accessible to FTSC. Each value represents the average of two parallel experiments.

Example 4

Effect of Protein Concentration on the Number of Aldehyde Groups Generated on IgG To determine the effect of protein concentration on the number of aldehyde groups generated by periodate oxidation, 0.5 ml of IgG solution at concentrations of 1.0, 2.0, and 4.0 mg/ml protein, in duplicate, was incubated with 20 µl of 0.25M $NaIO_4$ for 30 minutes in the dark. Each solution was then processed in the same manner as described above in Example 3.

As is shown in Table 3, the number of aldehyde groups that were generated from an IgG molecule remained constant at various IgG concentrations.

TABLE 3

Effect of IgG concentration on the oxidation efficiency of $NaIO_4$

| concentration of IgG (mg/ml) | number of —CHO groups generated |
|---|---|
| 1.0 | 0 |
| 2.0 | 1.3 |
| 4.0 | 1.5 |

1) Number of —CHO groups on an average IgG molecule which were accessible to FTSC. Each value represents the average of two parallel experiments.

Example 5

Conjugation of IgG to ALP

Four mg of monoclonal anti-BE IgG in 1.0 ml NaAc buffer was incubated in the dark with 20 µl of 0.5M $NaIO_4$ (in distilled water) for 30 minutes. The solution was desalted according to manufacturer's instructions to remove unreacted $NaIO_4$. The desalted IgG solution was added to an adipic dihydrazide solution (40 mg in 0.5 ml NaAc buffer) while stirring as above and the mixture was incubated at RT with stirring for 2 hours. The solution was desalted to remove excess adipic dihydrazide using NaAc elution buffer. Fractions with the highest concentration of protein were pooled and adjusted to a concentration of 1.075 mg/ml (2.0 ml total) in NaAc buffer.

30 µl of 0.5M $NaIO_4$ (in distilled water) was added to 1.5 ml of 2.0 mg/ml ALP (in NaAc buffer). The solution was incubated in the dark for 30 minutes, then desalted as above to remove unreacted $NaIO_4$. Eluted fractions were pooled and adjusted to a protein concentration of 1.0 mg/ml in NaAc buffer. ALP was conjugated to IgG by adding 1.0 ml of the above 1.075 mg/ml IgG to 1.0 ml of the newly prepared 1.0 mg/ml ALP. The solution was incubated at 4° C. for 18 hours with gentle head-over-head mixing. The ALP—IgG conjugate was purified by gel filtration using Sephacryl S-200-HR media/150 mM NaCl/50 mM sodium phosphate, pH 7.0 buffer.

Example 6

ELISA Assay of Cocaine Using the New ALP—IgG Conjugate

A competitive BE ELISA was performed on a BE—BSA (1 µg/ml) coated microtiter plate. 50 µl of ALP—IgG conjugate (~3.0 µg/ml in PBS/1.0% BSA) was added to each well and the plate was incubated for one hour at 37° C. The wells were washed with 0.1% Tween-20/PBS. 50 µl of the following concentrations of BE (diluted in 1.0% BSA/PBS) were tested: 500, 250, 125, 62.5, 31.25, 15.6, 7.8 and 3.9 ng/ml. The plate was incubated for one hour at 37° C. After washing with 0.1% Tween-20/PBS, 50 µl of 2.0 mg/ml p-nitrophenol phosphate (in 1.0M diethanolamine, pH 9.8) was added to each well. The plate was incubated at RT for 15 minutes after which the reaction was stopped by adding 50 µl of 3N NaOH to each well. The absorbance of each well was read at 405 nm. The results of the assay are shown in FIG. 1. The error bars represent the O.D. difference between two parallel experiments. The results of the ELISA show that BE bound in a dose dependent manner to the ALP—IgG conjugate indicating that the IgG-enzyme conjugate obtained using the method of the present invention retained its ability to bind to its antigen.

I claim:

1. A method for the site-specific covalent conjugation of an enzyme and an antibody through carbohydrate residues, comprising:

(a) contacting an enzyme with an oxidizing reagent, said reagent being present in a greater than a 1:1 molar ratio amount to the molar amount of enzyme present, to generate an aldehyde group on the enzyme;

(b) contacting an antibody with an oxidizing reagent, said reagent being present in a greater than a 1:1 molar ratio amount to the molar amount of antibody present, to generate an aldehyde group on the antibody;

(c) contacting the antibody-aldehyde of step (b) with a molar excess of a dihydrazide or dihydrazine containing compound to form a hydrazone bond between the aldehyde group of the antibody-aldehyde and a hydrazide or hydrazine group of the dihydrazide or dihydrazine containing compound to form an antibody-hydrazide or antibody-hydrazine intermediate;

(d) removing excess unreacted dihydrazide or dihydrazine containing compound from the mixture of step (c);

(e) contacting the antibody-hydrazide or antibody-hydrazine conjugate from step (d) with the enzyme-aldehyde of step (a), to form a second hydrazone bond between the aldehyde group of the enzyme-aldehyde and an unreacted hydrazide or hydrazine group of the dihydrazide or dihydrazine containing compound thereby generating an antibody-enzyme conjugate.

2. The method of claim 1 wherein the oxidizing reagent is sodium periodate.

3. The method of claim 2 wherein the sodium periodate is at a concentration of from about 0.01 to about 500 mM.

4. The method of claim 3 wherein the concentration of sodium periodate is 10 mM.

5. The method of claim 1 wherein the pH of the oxidation reaction mixture of steps (a) and (b) is at a range of from about 5.0 to about 6.0.

6. The method of claim 5 wherein the pH is about 5.5.

7. The method of claim 1 wherein the time for the oxidizing reaction of steps (a) and (b) is from about 1 minute to about 2 hours.

8. The method of claim 7 wherein oxidation occurs for about 30 minutes.

9. The method of claim 1 wherein the dihydrazide or dihydrazine containing compound is a compound selected from adipic dihydrazide, succinic dihydrazide and 1,6-hexyldihydrazine.

10. The method of claim 9 wherein the dihydrazide or dihydrazine containing compound is adipic dihydrazide.

11. A method for the site specific conjugation of two or more glycoproteins through carbohydrate residues on the glycoproteins, comprising:

(a) contacting a first glycoprotein with an oxidizing reagent, said reagent being present in an amount which is greater than a 1:1 molar ratio to the molar amount of glycoprotein present, to generate an aldehyde on the first glycoprotein;

(b) removing excess oxidizing reagent from the reaction mixture of step (a);

(c) contacting the first glycoprotein of step (b) with a dihydrazide- or dihydrazine-containing reagent, said reagent being present in a molar amount in excess over the amount of oxidized glycoprotein present, to form a hydrazone bond between the aldehyde on the glycoprotein and a first hydrazide or hydrazine on the dihydrazide or dihydrazine reagent, thereby generating a glycoprotein-hydrazide or glycoprotein-hydrazine intermediate;

(d) removing excess dihydrazide- or dihydrazine containing reagent from the mixture of step (c);

(e) contacting a second glycoprotein and an oxidizing reagent, said reagent being present in an amount which is greater than a 1:1 molar ratio amount to the molar amount of glycoprotein present, to form an aldehyde group on the second glycoprotein;

(f) removing excess oxidizing reagent from the mixture of step (e);

(g) contacting the glycoprotein-hydrazide or glycoprotein-hydrazine intermediate of step (d) with the second glycoprotein of step (f) to form a second hydrazone bond between the aldehyde on the second glycoprotein and an unreacted hydrazide or hydrazine of the dihydrazide or hydrazine reagent; and (h) blocking unreacted hydrazide or hydrazine groups, thereby generating a glycoprotein-glycoprotein conjugate.

12. A method for the site specific conjugation of two or more glycoproteins through carbohydrate residues on the glycoproteins, comprising:

(a) contacting a first glycoprotein with an oxidizing reagent, said reagent being present in an amount which is greater than a 1:1 molar ratio to the molar amount of glycoprotein present, to generate an aldehyde on the first glycoprotein;

(b) removing excess oxidizing reagent from the reaction mixture of step (a);

(c) contacting the first glycoprotein of step (b) with a dihydrazide- or dihydrazine-containing reagent, said reagent being present in a molar amount in excess over the amount of oxidized glycoprotein present, to form a hydrazone bond between the aldehyde on the glycoprotein and a first hydrazide or hydrazine on the dihydrazide or dihydrazine reagent, thereby generating a glycoprotein-hydrazide or glycoprotein-hydrazine intermediate;

(d) removing excess dihydrazide- or dihydrazine containing reagent from the mixture of step (c);

(e) contacting a second glycoprotein and an oxidizing reagent, said reagent being present in an amount which is greater than a 1:1 molar ratio amount to the molar amount of glycoprotein present, to form an aldehyde group on the second glycoprotein;

(f) removing excess oxidizing reagent from the mixture of step (e);

(g) contacting the glycoprotein-hydrazide or glycoprotein-hydrazine intermediate of step (d) with the second glycoprotein of step (f) to form a second hydrazone bond between the aldehyde on the second glycoprotein and an unreacted hydrazide or hydrazine of the dihydrazide or hydrazine reagent; and (h) blocking unreacted hydrazide or hydrazine groups, thereby generating a glycoprotein-glycoprotein conjugate.

* * * * *